United States Patent [19]
Knox

[11] 4,306,862
[45] Dec. 22, 1981

[54] DENTAL BURR TOOL BLOCK ASSEMBLY

[76] Inventor: Kathleen K. Knox, 312 Ranchwood Manor Dr., Oklahoma City, Okla. 73139

[21] Appl. No.: 178,997

[22] Filed: Aug. 18, 1980

[51] Int. Cl.³ ............................................. A61C 1/14
[52] U.S. Cl. ................................. 433/77; 206/63.5; 206/210
[58] Field of Search .................... 433/77, 79; 206/63.5, 206/368, 369, 379, 210; 422/102, 104

[56] References Cited

U.S. PATENT DOCUMENTS

| | | | |
|---|---|---|---|
| 602,103 | 4/1898 | Place | 433/77 |
| 816,959 | 4/1906 | Briganti | 206/210 |
| 1,104,650 | 7/1914 | Fries | 206/210 |
| 1,135,625 | 4/1915 | Savin | 433/77 |
| 1,437,596 | 12/1922 | Korb | 206/369 |
| 1,446,921 | 2/1923 | Montag | 206/369 |
| 2,375,645 | 5/1945 | Gordon | 206/63.5 |
| 3,092,443 | 6/1963 | Dietz | 433/77 |
| 3,270,416 | 9/1966 | Massa | 433/77 |
| 3,358,826 | 12/1967 | Siegel | 206/368 |
| 3,451,133 | 6/1969 | Hathaway et al. | 433/77 |

FOREIGN PATENT DOCUMENTS

| | | | |
|---|---|---|---|
| 94773 | 11/1923 | Fed. Rep. of Germany | 206/369 |
| 2268437 | 11/1975 | France | 433/79 |
| 2037256 | 4/1980 | United Kingdom | 433/77 |

OTHER PUBLICATIONS

"Plastic Drill Cases", Rogers, Modern Packaging, Jul. 1947, p. 115.

*Primary Examiner*—Robert Peshock
*Assistant Examiner*—John J. Wilson
*Attorney, Agent, or Firm*—Dennis T. Griggs

[57] ABSTRACT

A dental burr tool block in which a plurality of bore openings are provided for receiving and storing a variety of dental burr tools. Machined from the block is a reservoir compartment capable of holding a volume of disinfectant fluid, a drain hole at the bottom of the reservoir compartment, and a receptacle for receiving and holding in place a burr changer tool. The top surface of the block is protected by a pivotally mounted transparent dust cover, with the dust cover being removably connected to the block by means of two inwardly directed shafts. The shafts are connected to the dust cover and inserted into bore openings in the block.

2 Claims, 3 Drawing Figures

DENTAL BURR TOOL BLOCK ASSEMBLY

BACKGROUND OF THE INVENTION

1. Field of the Invention

This invention relates to a dental tool block for dental drill bits, burrs and similar drill-rotated instruments. More particularly, the invention relates to a holder for receiving and storing the tools ordinarily employed by a dentist in the drilling, cutting or polishing of teeth, and for promoting sanitation in the use and storage of such tools.

2. Description of the Prior Art

It is customary for a dentist to use a power driven hand piece which carries a rotary chuck in which the stem or shank portions of various dental tools are inserted. Prior designs for such a dental hand piece incorporated the use of a friction fitting in the rotary chuck for holding the dental tools. However, as the friction fitting had resulted in some problems in holding the tools in place, improved hand pieces have been designed to incorporate a rotary chuck which is tightened through use of a burr changer tool. This burr changer tool is quite small and, as a result of its size, often gets inadvertently discarded during the clean-up and preparations done prior to beginning work on a new patient. At present, the existing structures which facilitate storage of, and easy access to, the dental tools do not provide any means for keeping track of a burr changer tool, nor do they afford any means for sanitary storage of the used dental tools during operation.

Dental holders, whereby the dental tools stored therein can be easily removed and installed in the friction fitting of a dentist's power driven hand piece while using only one hand, are described in U.S. Pat. Nos. 3,451,133 and 3,270,416.

In the burr tool holder according to U.S. Pat. No. 3,451,133, an annular outwardly opening, peripheral groove is provided in the base, forming a shelf upon which the dental tools rest. This open groove provides a means by which the dentist can view the working-tip when making his selection of tools. The base also supports a magnetic means which attracts and retains the used dental tools when they are removed from the friction fitting of a dentist's power driven hand piece.

In the burr tool holder according to U.S. Pat. No. 3,270,416, tubular members extending through the circular apertures in the top edge of a hollow wall rest upon a ledge inside the wall, defining a plurality of receptacles for burr storage. One-handed installation of the burr tools in the riction fitting of a dentist's power driven hand piece is accomplished through use of a plurality of spring-loaded dispenser units. These dispenser units are separately connected to the base and extend vertically upward therefrom.

In U.S. Pat. No. 602,103, a dental storage cabinet is shown comprised of a plurality of hollow, pie-shaped compartments. To the cabinet is mounted a circular cover plate with a hinged, pie-shaped door connected thereto. This cover plate can be rotated around the central axis of the circular base so that the pie-shaped door can be lifted to expose any one of the pie-shaped compartments in the base.

In U.S. Pat. No. 1,434,793, a dentist's central tool station is shown which shows, but does not teach or claim, a pivoted support plate of the type which could hold a burr tool holder.

SUMMARY OF THE INVENTION

The improved dental burr tool block assembly of this type according to the present invention is characterized by a main body structure comprised of a single block of material which has been machined to include a reservoir compartment, a drain hole and bore openings. The simplicity of design, as well as the limited number of parts, make the structure much easier to assemble and more economical to mass produce than the dental holders taught in the prior art.

The reservoir compartment provides a container for a volume of disinfectant fluid which allows the dentist to set aside used burr tools while easily maintaining the desirable hygienic conditions. A removable transparent dust cover is pivotally mounted on the block so that the top surface of the block is protected against dust and other foreign objects while still providing easy access to the surface when the dust cover is rotated back. The dust cover is made of a resilient material so that it can be easily removed from the base. The drain hole at the bottom of the reservoir compartment is sealed with a removable drain plug which, when removed along with the dust cover, allows the dentist to sterilize the block and any remaining unused burr tools without requiring the prior removal of the burr tools from the block.

DESCRIPTION OF THE PREFERRED EMBODIMENT

Figure 1:
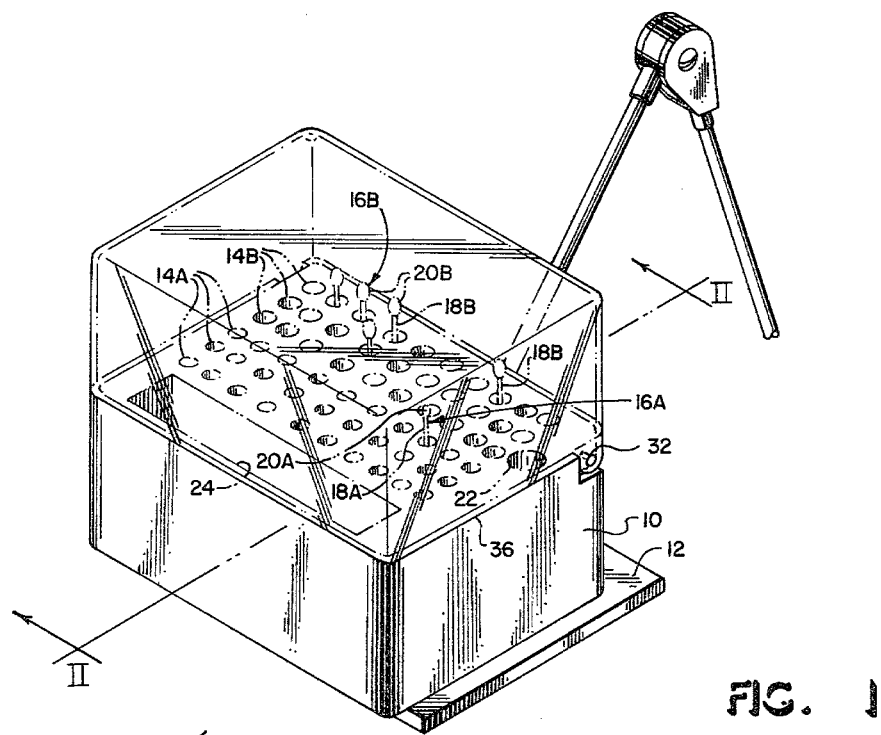
FIG. 1 is a perspective view of the dental burr tool holder with the dust cover down in its sealing position.

Referring now to FIG. 1 of the drawings, a single block of mterial (10) is shown supported by an adjustable shelf (12) of the type which is typically attached to a dentist's central power tool station (not shown). The block has been machined to include a plurality of bore openings (14A, 14B) which are capable of receiving and storing dental burr tools (16A, 16B). The bore openings (14A, 14B) have been machined to such a depth that the shanks (18A, 18B) of the burr tools (16A, 16B) will project above the block (10) so as to facilitate their easy removal. The storage of these burr tools (16A, 16B) is best illustrated in FIG. 2 which shows the placement of the burr tools (16A, 16B) with the working-tips (20A, 20B) projecting above and the shanks (18) projecting below the surface of the block (10).

The single block of material (10) facilitates ease of manufacture with attendant cost savings due to the simplicity of design, and is made completely of durable materials, for example, a metal such as aluminum or a polymer such as nylon, which can withstand, without substantial deformation, sterilization by autoclave, boiling or cold solution. Thus, the entire block (10) with burr tools (16A, 16B) in place, can be sterilized at one time.

The block (10) is provided with a receptacle (22) for receiving and removably holding in place a burr changer tool (not shown) of a type that is typically used by dentists in the installation and removal of the burr tools (16A, 16B) from their power driven hand pieces. This receptacle keeps the burr changer tool from being inadvertently misplaced and/or discarded when not in use.

Figure 2:
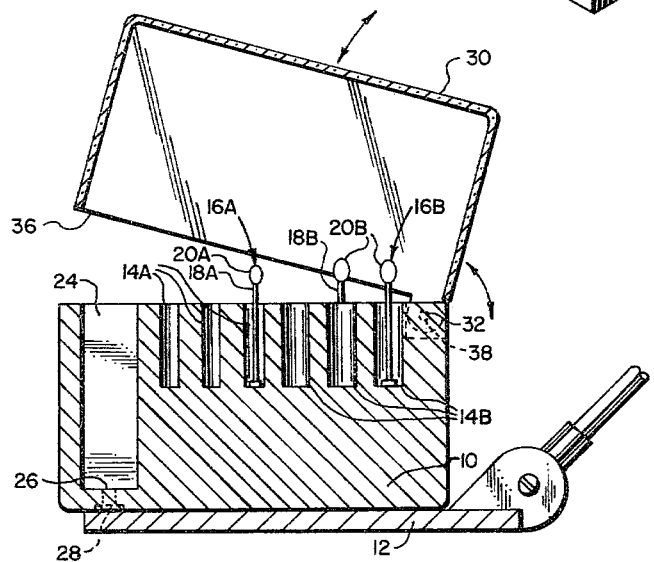
FIG. 2 is a side cross-sectional view of the dental burr tool holder seated on a typical support shelf showing the dust shelf being pivoted back to allow access to the surface of the block.

Referring to FIG. 2, the block (10) is shown having a reservoir compartment (24) machined out of the block (10) which is capable of holding a volume of disinfectant fluid. As the burr tools (16A, 16B) are used, they may be removed from the dentist's power driven hand piece and dropped into the disinfectant fluid in this reservoir compartment (24), thereby greatly enhancing the sanitary conditions surrounding the use of such burr tools (16A, 16B). The block (10) is shown having a drain hole (26) which extends from the bottom of the reservoir compartment (24) through the bottom of the block (10). During use, the drain hole (26) is sealed with a removable water-tight plug (28). Thereafter, when the dentist desires to drain the reservoir compartment (24), the water-tight plug (28) can be removed, enabling the disinfectant fluid to drain out of the drain hole (26) without requiring removal of the unused burr tools (16) from the bore openings (14A, 14B).

A removable transparent dust cover (30) is pivotally mounted on the block (10) by means of inwardly directed horizontal shafts (32) connected to the lower rear side edges (34) of the dust cover (30). The shafts are inserted into side bore openings (38) in the block (10). When in use, the dust cover (30) can be pivoted on the inwardly directed horizontal shafts (32) between two basic positions. In the first position (see FIG. 1), the dust cover (30) is in a resting position of engagement with the top of the block (10), with the lower edges (36) of the dust cover (30) forming a seal around the periphery of the block (10). When access to the top surface of the block (10) is desired, the dust cover (30) can be pivoted back out of the way (see FIG. 2) so as to allow convenient access to the burr tools in storage.

The dust cover (30) comprises a resilient material which allows the lower rear side edges (34) of the dust cover (30) to be manually deflected outwardly, thus removing the inwardly-directed shafts (32) from the side bore openings (38) in the block (10). This allows the removal of the dust cover (30) from the block (10) whenever the block (10) is to be sterilized.

The entire block (10) can be fully loaded with burr tools (16A, 16B), sterilized, and then maintained in a sterile condition when the dust cover (30) is in place as shown in FIG. 1. Although the reservoir compartment (24) would normally be filled with disinfectant fluid in preparation for the dentist just prior to use, there is typically a brief waiting period between the time of such preparation and the actual use by the dentist. During this delay, the dust cover (30) also protects the disinfectant fluid in the reservoir compartment (24) from contamination with dust or other foreign objects, thus preserving the disinfecting qualities of the fluid.

When it is desired to use the burr tools (16A, 16B), the dust cover (30) can be pivoted back as shown in FIG. 2. The dentist may now select a particular burr tool by visual reference to any system of labeling or orgainzing the burr tools (16A, 16B) that may be desired.

Figure 3:
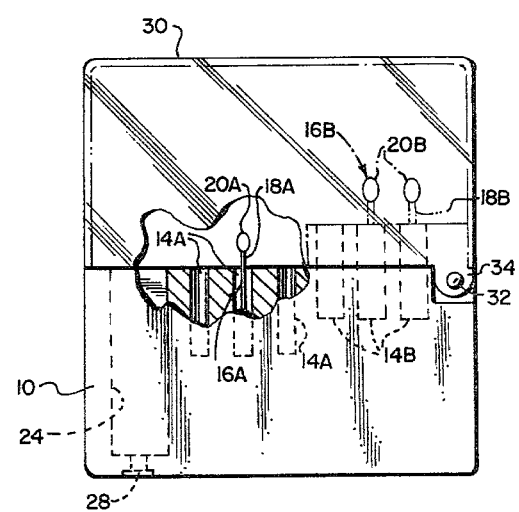
FIG. 3 is a side elevational view of the dental burr tool holder showing an alternative stepped configuration for the surface of the block.

One such system of organizing the burr tools (16A, 16B) is shown in FIG. 3. The upper surface of the block (10) can be machined to comprise any desired number of steps, each step containing a plurality of bore openings (14A, 14B) for holding a set of burr tools (16A, 16B) with a particular type of working-tip (20A, 20B). For example, bore openings (14A) have a relatively small diameter for receiving high speed tools (16A), and bore openings (14B) have a relatively larger diameter for receiving low speed tools (16B).

The main body of the structure is completely comprised of a single block of material which has been machined to include a compartment, drain hole and bore openings. The simplicity of design, as well as the limited number of parts, makes the structure much less expensive to manufacture than the devices taught in the prior art. It will be apparent that the structure described provides a convenient holder for dental burr tools which allows easy access to them when selected by a dentist. These instruments are supported with their burr portions upright so that the dentist can readily identify them.

The reservoir compartment allows the dentist to set aside used burr tools while easily maintaining the desirable hygienic conditions. By placing the burr changer tool in its receptacle after each use, the dentist will never have to spend time searching for a changer tool which has been inadvertently misplaced or discarded. The removable dust cover and the drain plug allow the dentist to thereafter sterilize the block, and any remaining unused burr tools, without requiring the prior removal of the burr tools from the block. Furthermore, after this sterilization, the dust cover can be put back into place in order to maintain the sanitary condition of the burr tools, disinfectant fluid and block until the dentist is ready to use them.

What is claimed is:

1. A dental burr tool holder comprising, in combination:

a single block of material capable of withstanding, without substantial deformation, exposure to high temperatures during sterilization processes, said block having a plurality of bore openings capable of receiving and storing dental burr tools, said openings being machined to such a depth that the tools will project far enough above the block so as to facilitate their easy removal without having to touch their work-tips;

said block having a compartment defining an open reservoir for containing a volume of disinfectant fluid which will provide an easy means of disinfecting the burr tools after they are used, said compartment extending downward from the top surface of the block;

said block having a drain hole which extends from the bottom of said reservoir compartment through the bottom of the block in order to facilitate removal of the disinfectant fluid;

said block having a removable water-tight plug installed for sealing the drain hole;

said block having a receptacle for receiving a burr changer tool;

a removable transparent dust cover pivotally mounted on said block, said dust cover being movable from a first resting position of engagement with the top of said block in which it forms a seal along the periphery of said block, to a second resting position providing easy access to burr tools stored in said block;

said dust cover having inwardly directed shafts connected to the lower rear side edges of said dust cover;

said block having side bore openings capable of receiving said inwardly directed shafts; and, wherein said dust cover comprises a resilient material thereby allowing deflection of said lower rear side edges for the removal of said inwardly directed shafts from said block.

2. A dental burr tool holder, comprising:

a single block of aluminum having a plurality of bore openings capable of receiving and storing dental burr tools, said openings being machined to such a depth that the tools will project far enough from the block so as to facilitate their easy removal without having to touch their working-tips;

wherein the upper surface of said block is stepped to provide easy access to a plurality of different levels;

said block having a compartment which defines an open reservoir for containing a volume of disinfectant fluid which will provide an easy means of disinfecting the burr tools after they are used, said compartment extending downward from the top surface of the block;

said block having a drain hole which extends from the bottom of said reservoir compartment through the bottom of the block in order to facilitate removal of the disinfectant fluid;

said block having a removable water-tight plug installed for sealing the drain hole;

said block having a receptacle for receiving a burr changer tool;

a removable transparent dust cover pivotally mounted on said block, said dust cover being movable from a first resting position of engagement with the top of said block in which it forms a seal along the periphery of said block, to a second resting position providing an easy access to burr tools stored in said block;

said dust cover having inwardly directed shafts connected to the lower rear side edges of said dust cover;

said block having side bore openings capable of receiving said inwardly directed shafts; and wherein said dust cover comprises a resilient material thereby allowing deflection of said lower rear side edges for the removal of said inwardly directed shafts from said block.

* * * * *